United States Patent [19]
Horzewski et al.

[11] Patent Number: 5,364,376
[45] Date of Patent: Nov. 15, 1994

[54] CONVERTIBLE CATHETER

[75] Inventors: Michael J. Horzewski; Jeffrey L. Kraus, both of San Jose, Calif.

[73] Assignee: Danforth Biomedical Incorporated, Menlo Park, Calif.

[21] Appl. No.: 926,530

[22] Filed: Aug. 4, 1992

[51] Int. Cl.⁵ .............................................. A61M 25/00
[52] U.S. Cl. .................................... 604/280; 604/53; 604/247
[58] Field of Search .......................... 604/164, 96–103, 604/280, 52, 53, 181, 269, 249, 256, 266, 267, 264, 247; 606/194, 27–29, 192, 198; 128/656, 657, 658, 772

[56] References Cited

U.S. PATENT DOCUMENTS

| | | | |
|---|---|---|---|
| 4,552,554 | 11/1985 | Gould | 604/51 |
| 4,643,712 | 2/1987 | Kulik et al. | 604/4 |
| 4,657,536 | 4/1987 | Dorman | 604/247 |
| 4,748,982 | 6/1988 | Horzewski et al. | |
| B1 4,762,129 | 7/1991 | Bonzel | 606/194 |
| 4,762,129 | 8/1988 | Bonzel | |
| 5,040,548 | 8/1991 | Yock | 128/898 |
| 5,135,535 | 8/1992 | Kramer | 606/194 |
| 5,171,222 | 12/1992 | Euteneuer et al. | 604/102 |
| 5,180,364 | 1/1993 | Ginsburg | 604/53 |
| 5,234,407 | 8/1993 | Teirstein et al. | 604/53 |

FOREIGN PATENT DOCUMENTS

| | | | |
|---|---|---|---|
| 0282143 | 1/1988 | European Pat. Off. | A61M 25/00 |
| 0380873 | 12/1989 | European Pat. Off. | A61M 29/02 |
| 9211894 | 7/1992 | WIPO | 604/194 |

*Primary Examiner*—C. Fred Rosenbaum
*Assistant Examiner*—V. Alexander
*Attorney, Agent, or Firm*—David H. Jaffer

[57] ABSTRACT

The present invention is a catheter having a guidewire lumen slidable sleeve. The lumen and sleeve have aligned apertures, which may be closed by moving the slidable sleeve. When the apertures are aligned, a guidewire may be loaded from the distal end of the catheter through the lumen. The guidewire is forced out of the lumen by a ramp in the lumen. The ramp is at the end of a removable core member, which provides enhanced shaft rigidity. The catheter may be converted from a "monorail" to an "over-the-wire" configuration by moving the slidable sleeve to close the aperture and advancing a replacement guidewire through the guidewire lumen past the now sealed aperture. A non-circular cross-section is used for the lumen, removable core member, and slidable sleeve, thereby maintaining orientation of the lumen and slidable sleeve apertures should the catheter undergo rotational flexing during use.

25 Claims, 4 Drawing Sheets

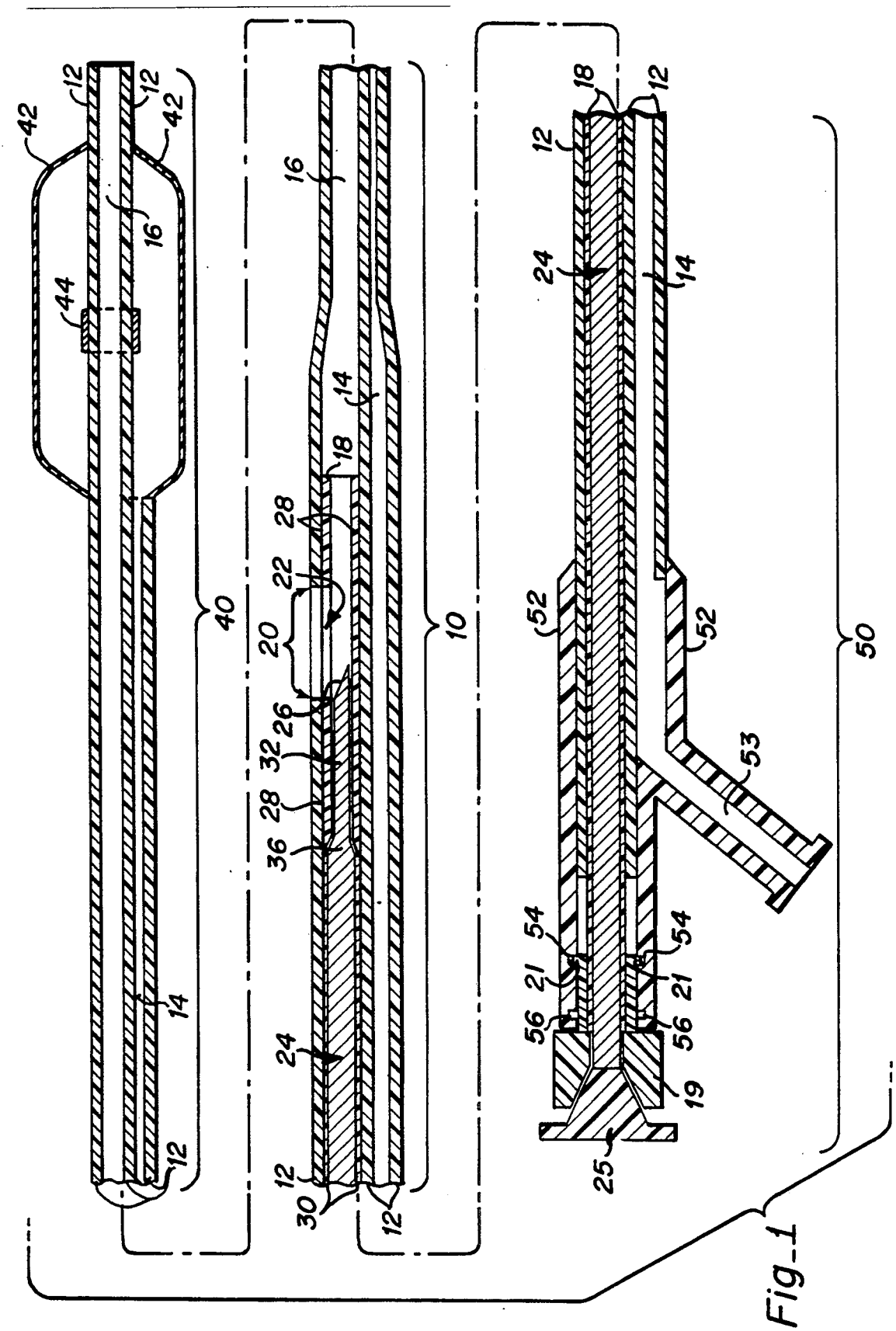

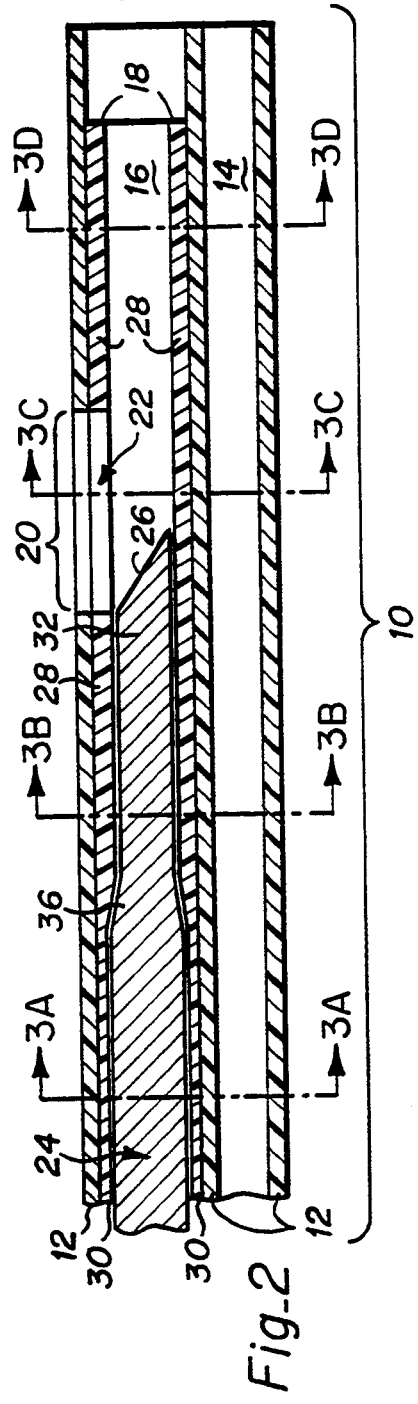
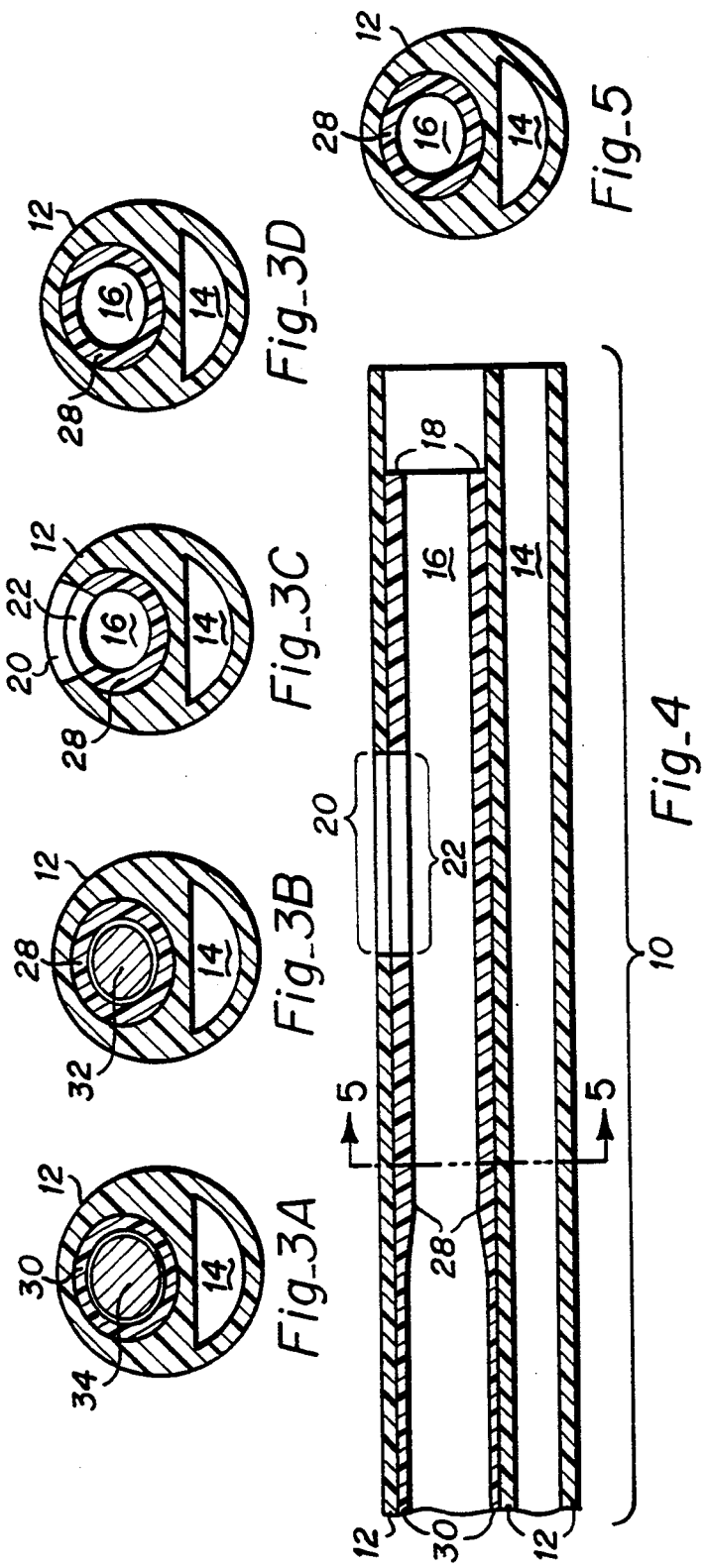

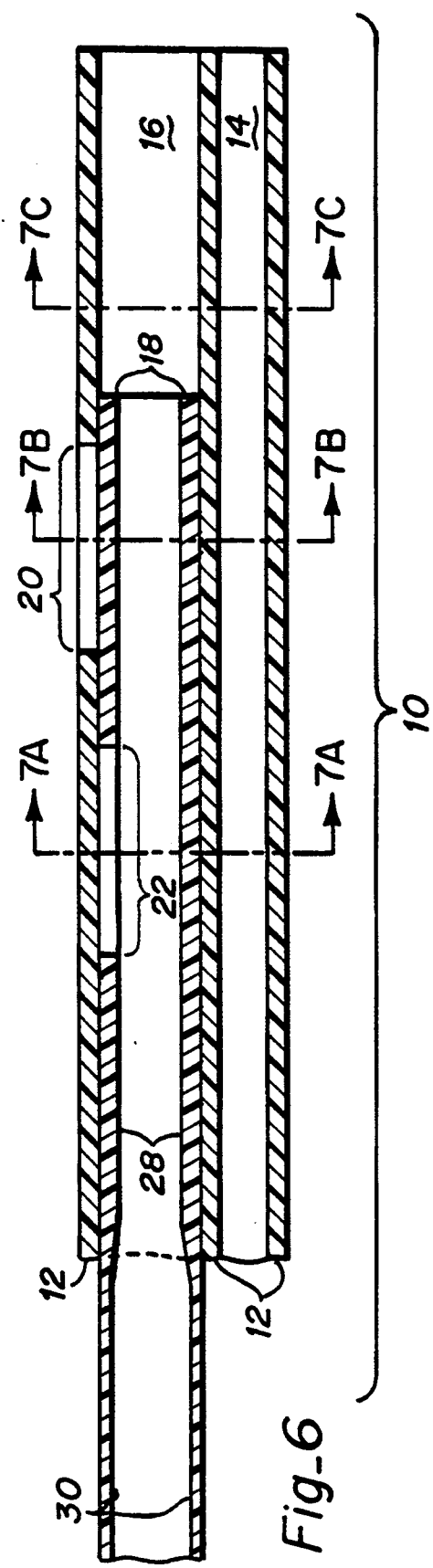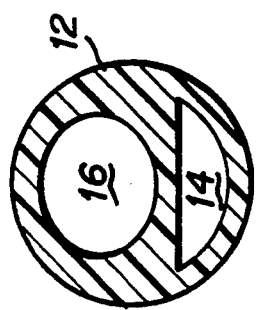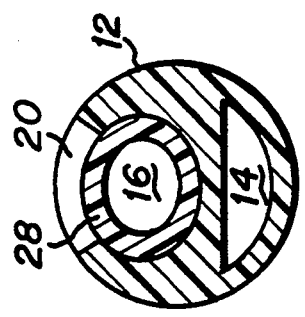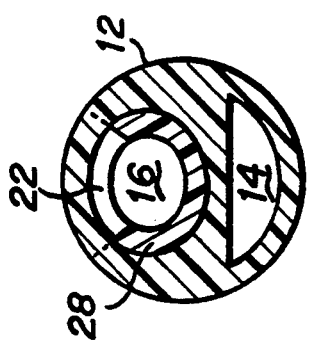

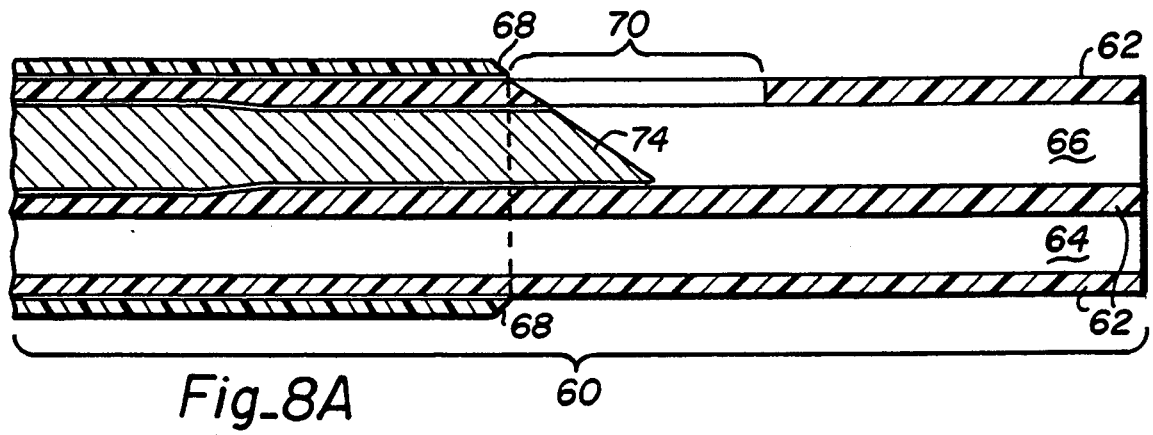
Fig_8A
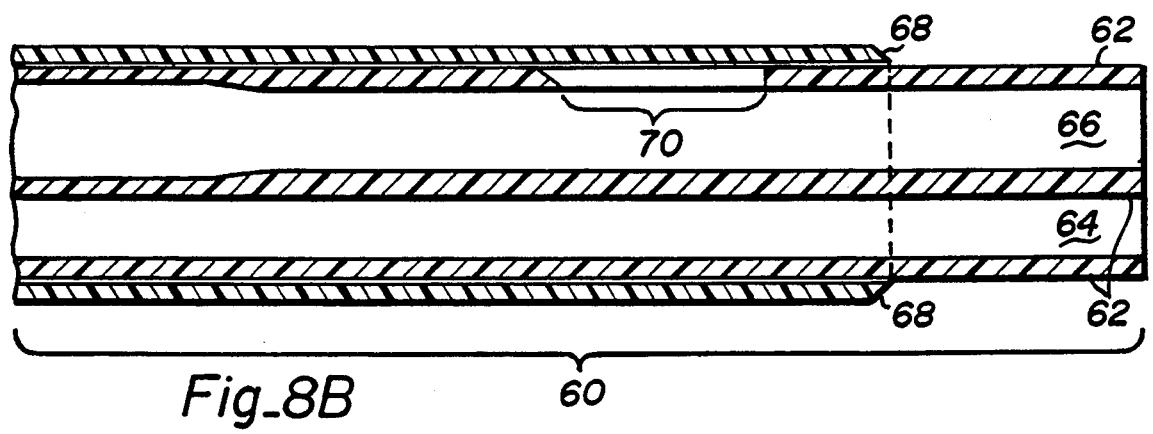
Fig_8B
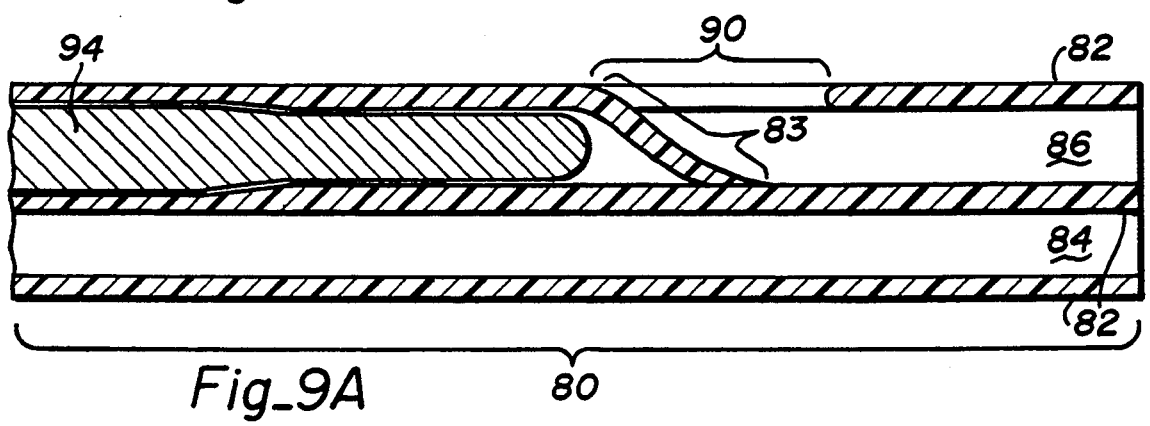
Fig_9A
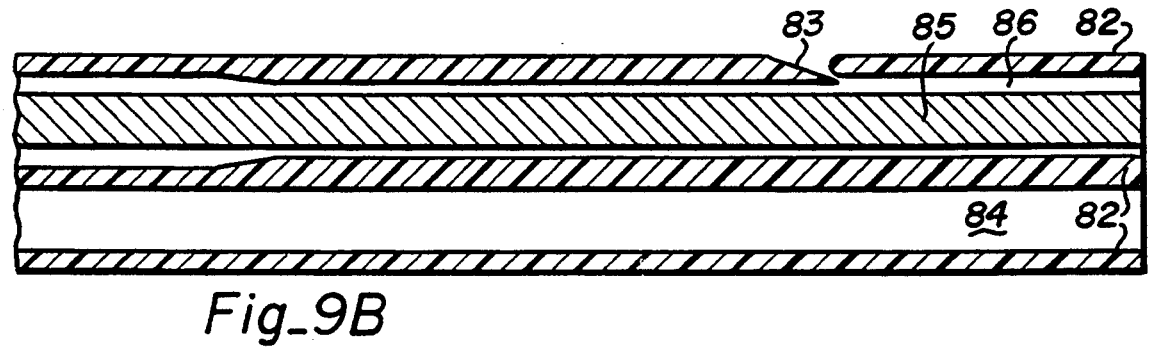
Fig_9B

CONVERTIBLE CATHETER

BACKGROUND OF THE INVENTION

1. Field of the Invention

This invention relates generally to an exchangeable catheter, and more particularly to a catheter which is convertible from one which permits simple and rapid exchange of catheters while a guidewire is in place to a catheter which allows guidewires to be exchanged while the catheter is in place.

2. Brief Description of the Prior Art

Various configurations of catheters and guidewires have been developed over the years for the purpose of satisfying different functional requirements. "Over-the-wire" catheter systems permit full rotational and full coaxial mobility of the guidewire relative to the catheter component of the system. "Over-the-wire" catheters can be fully withdrawn over a guidewire, and they will accept the antegrade and retrograde introduction of a guidewire therethrough. U.S. Pat. No. 4,323,071 describes an "over-the-wire" system.

While "over-the-wire" systems allow for exchange of catheters along the fixed guidewire and vice versa, such replacement is mechanically difficult because "over-the-wire" systems require that the guidewire protrude from the patient's body by a length greater than the length of the catheter. Thus, manipulation of the catheter during catheter replacement is difficult.

A different type of catheter-guidewire system has been developed to address this problem. Known generically as "rapid exchange" or "monorail" catheters, the design permits catheter exchange over a standard 175 cm length guidewire. U.S. Pat. Nos. 4,762,129 to Bonzel, 4,748,982 to Horzewski et al., and 5,040,548 to Yock teach variations of such designs. The designs include an inflation lumen within the catheter which runs the length of the catheter, and a separate guidewire lumen which extends a relatively short distance from the distal end toward the proximal end of the catheter. Since the guidewire lumen is relatively short compared to the overall length of the catheter, when one catheter is withdrawn over the guidewire and replaced with another guidewire, only the relatively short guidewire lumen needs to be threaded over the fixed guidewire.

The "monorail" concept has been readily accepted because it permits simple and rapid catheter exchange. However, a major problem of the design is that once a "monorail" catheter has been positioned, the guidewire is extremely difficult to exchange. This is because the guidewire lumen is relatively short. When the catheter is in place and the guidewire is withdrawn, it is impractical to locate the guidewire lumen with a replacement guidewire while the "monorail" catheter (and entrance to the guidewire lumen) is within a patient's body.

SUMMARY OF THE INVENTION

It is a primary objective of the present invention to provide a convertible catheter design which allows the catheter to change configuration from one which can be exchanged over a standard 175 cm length guidewire to an "over-the-wire" catheter which allows guidewires to be exchanged while the catheter is in place. The design similarly permits reintroduction of substitute catheters after guidewire exchange.

Another object of the present invention is to provide a slidable sleeve on the catheter which permits conversion from the "monorail" to "over-the-wire" concepts, through advancement, retraction, or rotation of the slidable sleeve.

A further object of the present invention is to provide catheter core member which enhances shaft rigidity and facilitates guidewire exiting when the catheter is threaded over the guidewire.

Briefly, the preferred embodiment of the present invention comprises a catheter having a guidewire lumen with a slidable sleeve. The lumen and sleeve have aligned apertures, which may be closed by retracting, advancing, or rotating the slidable sleeve. When the apertures are aligned, a guidewire may be loaded from the distal end of the catheter through the lumen. The guidewire is forced out of the lumen by a ramp or flap in the lumen. Preferably, the ramp is on the end of a removable core member, which provides enhanced shaft rigidity. This "monorail" configuration may be converted to an "over-the-wire" configuration by removing the first guidewire, withdrawing the core member, moving the slidable sleeve to close the aperture, and advancing a replacement guidewire through the lumen past the now sealed aperture. The lumen with aperture, removable core member, and slidable sleeve with aperture are preferably non circular in cross-section, to maintain orientation of the lumen and slidable sleeve apertures should the catheter undergo any rotational flexing during use.

The objects above and other objects and advantages of the present invention will no doubt become apparent to those skilled in the art after having read the following detailed description of the preferred embodiment which is contained in and illustrated by the various drawing FIGS.

IN THE DRAWINGS

FIG. 1 is a cross-sectional view of three segments of the preferred embodiment of this invention taken along the lengthwise axis of the device;

FIG. 2 is a cross-sectional view of a portion of the preferred embodiment of this invention taken along the lengthwise axis of the device, with the apertures in the guidewire lumen and slidable sleeve aligned to permit guidewire loading;

FIGS. 3(a), 3(b), 3(c), and 3(d) are cross-sectional views of the device shown in FIG. 2, taken along lines A—A, B—B, C—C, and D—D of FIG. 2 and perpendicular to the lengthwise axis of the device;

FIG. 4 is a cross-sectional view of the device shown in FIG. 1, with the core member removed;

FIG. 5 is a cross-sectional view of the device shown in FIG. 4, taken along line A—A of FIG. 4;

FIG. 6 is a cross-sectional view of the device shown in FIG. 2, with the slidable sleeve retracted so that the apertures in the guidewire lumen and slidable sleeve are offset, causing the lumen to be closed;

FIGS. 7(a), 7(b), and 7(c) are cross-sectional views of the device shown in FIG. 6, taken along lines A—A, B—B, and C—C of FIG. 6;

FIGS. 8(a) and 8(b) show an alternative embodiment of the present invention, in which the slidable sleeve is on the exterior of the catheter; and FIGS. 9(a) and 9(b) show a second alternative embodiment of the present invention, in which a flap is substituted for the slidable sleeve.

DETAILED DESCRIPTION OF THE PREFERRED EMBODIMENT

This invention provides a catheter device that is conveniently and dependably convertible from a "monorail" design, with its advantages of simple and rapid exchange, to an "over-the-wire" design which permits guidewire exchange. The design also permits reintroduction of "monorail" catheters after guidewire exchange, should this be desired. For simplicity, the invention is described below with specific reference to its preferred embodiment in a multilumen angioplasty catheter. However, the design is suitable to both coaxial and multilumen catheter designs, and may be applied to any type of catheter.

Referring now to FIG. 1 of the drawing, a distal portion 40 of a multilumen dilatation catheter is shown. The walls 12 of the catheter define an inflation lumen 14 and a guidewire lumen 16. Near the distal end of the catheter, an inflatable balloon 42 is attached to the walls 12 of the catheter. The location of the catheter within a patient's body may be detected through a radiographic technique which identifies metal band 44 which is located on the walls 12 of the catheter in an approximately central location of inflatable balloon 42.

With reference to FIGS. 1 and 2, a portion 10 of a multilumen catheter is shown. The catheter portion 10 is situated a convenient distance from the distal end of the catheter. In general, in an angioplasty catheter as known in the prior art, this catheter portion 10 would be located from 3 to 30 cm from the distal end of the catheter. However, the exact distance is not critical, provided that portion 10 shown is located a convenient distance from the distal end to permit trackability over the guidewire.

In FIG. 2, the distal end of the catheter extends beyond the right hand side of the drawing. The walls 12 of the catheter define inflation lumen 14 and guidewire lumen 16. Typical construction of catheters uses a variety of materials to provide the desired properties of flexibility and pushability. For example, high density materials are used for enhanced pushability and strength, while lower density materials provide more flexibility. Catheters may be composed of a combination of these materials in different proportions throughout the length of the catheter.

A slidable sleeve 18 is shown within guidewire lumen 16 in FIG. 2. Slidable sleeve 18 is formed of a lubricious material, such as high density polyethylene or fluorinated polymers, which allows the slidable sleeve to move relatively easily within the walls 12 of guidewire lumen 16. Slidable sleeve 18 may extend any length toward the distal end of the catheter. Walls 12 of the guidewire lumen 16 preferably are internally lubricious, to facilitate movement of slidable sleeve 18, while also being externally bondable, for example to permit affixation of inflatable balloon 42 shown in FIG. 1.

Referring again to FIG. 2, removable core member 24 is inserted in guidewire lumen 16 to provide enhanced "push" for the catheter. Typically, core member 24 would be comprised of a materials such as titanium, titanium alloys (e.g. nickel titanium), or stainless steel. Core member 24 tapers through a tapered portion 36 to a thinner portion 32. The tapering of core member 24 enhances its fit within slidable sleeve 18, which has a corresponding thinner portion 30 and thicker portion 28 to conform to the tapering of core member 24. The tapering of core member 24 and slidable sleeve 18 may be gradual or in a stairstep pattern, but only one tapering is shown in FIG. 2 for the sake of simplicity. Tapering of core member 24 and slidable sleeve 18 is done in a manner that transmits push from core member 24 to the catheter shaft.

Both catheter wall 12 and slidable sleeve 18 are cut to define catheter wall aperture 20 and slidable sleeve aperture 22, creating an exit opening from guidewire lumen 16. Removable core member 24, when positioned in guidewire lumen 16, terminates near apertures 20 and 22. When catheter wall aperture 20 and slidable sleeve aperture 22 are aligned as in FIG. 2, guidewire lumen 16 may be loaded with a guidewire from the distal end of catheter 10 (toward the right of FIG. 1) through guidewire lumen 16. When the guidewire contacts ramp 26 on the distal end of core member 24, the guidewire is directed out of the catheter through aligned apertures 22 and 20 in slidable sleeve 18 and catheter wall 12.

An advantage of the thickened portion 28 of slidable sleeve 18 is that this thickened portion 28 may be stiffened to provide greater ability to manipulate the aperture in the slidable sleeve for the purposes discussed below. It also improves the transition between the proximal and distal portions of the catheter shaft and throughout the aperture region. This is useful because the transition from the end of core member 24 to the more flexible portion of the catheter shaft immediately distal thereof can be severe. It is helpful to "reinforce" this region and smooth out the transition.

With reference to FIGS. 3(a), 3(b), 3(c), and 3(d), cross-sectional views of the device shown in FIG. 2 are shown, taken along lines A—A, B—B, C—C, and D—D of FIG. 2 and perpendicular to the lengthwise axis of the catheter.

FIG. 3(a) shows wall 12 of the catheter, in which are defined inflation lumen 14 and guidewire lumen 16. In FIG. 3(a), guidewire lumen 16 is filled with thinner portion 30 of slidable sleeve 18 and thicker portion 34 of removable core member 24. FIG. 3(b) shows a cross-section of the catheter somewhat closer to the distal end. Guidewire lumen 16 is filled now with thickened portion 28 of slidable sleeve 18, and thinner portion 32 of removable core member 24. FIG. 3(c) is taken at a portion of the catheter where catheter wall aperture 20 and slidable sleeve aperture 22 are aligned. Thus, guidewire lumen 16 is open to the exterior of the catheter. FIG. 3(d) shows a portion of the catheter closer to the distal end. In this case, thickened portion 28 of slidable sleeve 18 is located within guidewire lumen 16 defined by catheter wall 12.

FIG. 4 depicts catheter portion 10 after core member 24 has been removed. Guidewire lumen 16 is now open from the distal to the proximal end of the catheter. However, guidewire lumen 16 remains open to the exterior of the catheter because catheter wall aperture 20 and slidable sleeve aperture 22 are still aligned.

FIG. 5 shows a cross-sectional view of the catheter taken on the proximal side of apertures 20 and 22. Wall 12 of the catheter defines guidewire lumen 16 with thickened portion 28 of slidable sleeve 18 situated on the outer periphery of guidewire lumen 16.

With reference to FIG. 6, slidable sleeve 18 has been moved relative to the remainder of catheter portion 10. Slidable sleeve aperture 22 is no longer aligned with catheter wall aperture 20. This closes the opening in guidewire lumen 16 and permits a guidewire to be loaded from the proximal end of the catheter (at the left of FIG. 6) toward the distal end of the catheter. The order of removing core member 24 and moving slidable sleeve 18 may be reversed.

Now a replacement guidewire may be put into place without removing the catheter, and with certainty that guidewire lumen 16 provides a continuous path through the overall catheter length from proximal to distal end. FIGS. 7(a) and 7(b) illustrate this, showing that guidewire lumen 16 no longer has an opening because catheter wall 12 now covers slidable sleeve aperture 22, and thickened portion 28 of slidable sleeve 18 now covers catheter wall aperture 20. Thus, a guidewire may be threaded through the entire length of guidewire lumen 16, without risk that the guidewire will exit through what was formerly an opening in guidewire lumen 16 when slidable sleeve aperture 22 and catheter wall aperture 20 were aligned.

After a guidewire has been inserted in guidewire lumen 16 from the proximal to distal end of the catheter, the catheter serves as a "over-the-wire" catheter. Wires may be replaced easily through guidewire lumen 16. In the event that it should become necessary to substitute catheters, the catheter may be removed along the guidewire while maintaining the guidewire in place, in the standard "over-the-wire" manner. Once the catheter has been removed with the guidewire remaining in place, a new catheter may be substituted. This new catheter may be of the "monorail" or "over-the-wire" varieties, or may be a convertible catheter as taught by this invention.

It should be noted that the opening in guidewire lumen 16 may be closed either through retracting slidable sleeve 18 as shown in FIG. 6, or by advancing the slidable sleeve. In the preferred embodiment, guidewire lumen 16, slidable sleeve and removable core member 24 all have noncircular cross-sections which serve to maintain alignment of apertures 20 and 22, should the catheter undergo any rotational flexing during use. However, in an alternative embodiment the apertures in the guidewire lumen and slidable sleeve could be closed by rotating the sleeve with respect to the guidewire lumen, particularly their cross-sections are relatively circular.

Referring back to FIG. 1, a third portion 50 of the multilumen catheter is shown. Catheter portion 50 is the proximal end of the catheter. Portion 50 includes walls 12 of the catheter defining inflation lumen 14 and a guidewire lumen. The guidewire lumen (shown as 16 in portion 10 of the catheter) is filled with removable core member 24. Slidable sleeve 18 is shown extending to the proximal end of the catheter. The proximal portion 50 of the catheter terminates in a first fitting 52 adapted to serve several functions. First fitting 52 is attached to walls 12 of the catheter, and includes an inflation port 53 through which an inflation fluid may be added to inflation lumen 14 for inflating balloon 42.

Knob 25 is attached to removable core member 24 so that removable core member 24 may be easily removed from the catheter, leaving guidewire lumen 16 open and available for entry by a guidewire.

Second proximal fitting 19 is attached to slidable sleeve 18, permitting slidable sleeve 18 to be manipulated from the proximal end of the catheter. Second fitting 19 includes an annular ring 21 which fits into notch 54 in first fitting 52 when, as discussed above, slidable sleeve 18 is in a position such that catheter wall aperture 20 and slidable sleeve aperture 22 are aligned. Second fitting 19 may be compressed after core member 24 is removed, permitting annular ring 21 to be moved from notch 54 to notch 56, thereby moving slidable sleeve 18 with respect to catheter wall 12, misaligning catheter wall aperture 20 and slidable sleeve aperture 22, and closing guidewire lumen 16.

With reference to FIGS. 8(a) and 8(b), an alternative embodiment is shown. In this embodiment, catheter portion 60 is similar to catheter portion 10 shown in FIG. 2, except that the slidable sleeve is mounted on the exterior of the catheter walls. In FIG. 8(a), walls 62 of the catheter define inflation lumen 64 and guidewire lumen 66. Guidewire lumen 66 is filled with removable core member 74. Slidable sleeve 68 is exterior to catheter walls 12. As shown in FIG. 8(a), core member 74, catheter wall aperture 70, and slidable sleeve 68 are initially aligned to permit guidewire loading from the distal end of the catheter, as discussed above.

FIG. 8(b) shows catheter portion 60 after core member 74 has been removed, and catheter walls 62 and slidable sleeve 68 have been moved relative to each other, closing guidewire lumen 66 with respect to the exterior of the catheter. Thus, guidewire lumen 66 is now sealed, and a new guidewire may be advanced from the proximal to the distal end of guidewire lumen 66.

FIGS. 9(a) and 9(b) show another alternative embodiment of the invention. In FIG. 9(a), catheter portion 80 corresponds to catheter portion 10 shown in FIG. 2. FIGS. 9(a) and 9(b) show catheter walls 82, inflation lumen 84, guidewire lumen 86, and removable core member 94. FIG. 9(a) shows a flap portion 83 of catheter wall 82, which in FIG. 9(a) is situated to provide catheter wall aperture 90. In this configuration, flap 83 permits guidewire loading from the distal end of the catheter through guidewire lumen 86. Core member 94 reinforces flap 83, so that when a guidewire is loaded from the distal end of the catheter, the guidewire exits through catheter wall aperture 90.

If it is desired to convert the catheter to an over-the-wire type catheter, core member 94 is removed. FIG. 9(b) shows this embodiment after conversion to an over-the-wire type catheter. A guidewire 85 is loaded through the proximal end of the catheter, causing catheter flap portion 83 to be lifted to close guidewire lumen 86 to the exterior of the catheter. The material used for flap portion 83 preferably is a pliable material which when pressed against another portion of the catheter wall 82 adheres. In FIG. 9(a), flap portion 83 is attached to the catheter wall in a manner that keeps catheter wall aperture 90 open. Similarly, FIG. 9(b) shows that after flap portion 83 is forced upward by the force of guidewire 85, flap portion 83 closes guidewire lumen 86 to the exterior of the catheter, preferably adhering to the upper portion of catheter wall 82.

Although the present invention has been described in terms of specific embodiments, it is anticipated that alterations modifications thereof will no doubt become apparent to those skilled in the art. It is therefore intended that the following claims be interpreted as covering all such alterations and modifications as fall within the true spirit and scope of the invention.

What is claimed is:

1. A catheter adapted for reversible conversion from a rapid exchange configuration to an over-the-wire configuration, comprising:
   (a) a catheter having a guidewire lumen with proximal and distal apertures and an intermediate aperture situated between the proximal and distal apertures, whereby a guidewire may be loaded through the distal and intermediate apertures; and (b) movable means for closing the intermediate aperture, thereby permitting a guidewire to be loaded through the proximal aperture to the distal end of the guidewire lumen while preventing exit of the guidewire through the intermediate aperture.

2. The catheter of claim 1, wherein the means for closing the intermediate aperture comprises a sleeve which may be moved relative to the guidewire lumen, thereby closing and opening the intermediate aperture.

3. The catheter of claim 2, wherein the sleeve and the guidewire lumen have non-circular cross-sections.

4. The catheter of claim 2, wherein the proximal end of the sleeve is attached to a fitting, the fitting having a guide for indicating the relative positions of the sleeve and the guidewire lumen, thereby indicating when the intermediate aperture is open and closed.

5. The catheter of claim 2, wherein the sleeve lies inside the walls of the guidewire lumen.

6. The catheter of claim 2, wherein a portion of the sleeve is thickened, thereby providing greater ability to manipulate the sleeve.

7. The catheter of claim 2, wherein the sleeve is formed of a lubricious material.

8. The catheter of claim 2, wherein the sleeve lies outside the walls of the guidewire lumen.

9. The catheter of claim 1, wherein the means for closing the intermediate aperture comprises a flexible flap adjacent to the intermediate aperture.

10. The catheter of claim 1, further comprising a removable core member in the portion of the guidewire lumen proximal to the intermediate aperture.

11. The catheter of claim 10, wherein the means for closing the intermediate aperture comprises a flexible flap adjacent to the intermediate aperture.

12. The catheter of claim 10, wherein the distal end of the core member includes means for directing a guidewire out of the guidewire lumen through the intermediate aperture.

13. The catheter of claim 10, wherein the means for closing the intermediate aperture comprises a sleeve which may be moved relative to the guidewire lumen, thereby closing and opening the intermediate aperture.

14. A method for converting a catheter from a rapid exchange configuration to an over-the-wire configuration, comprising:

(a) loading a first guidewire through distal and intermediate apertures in a guidewire lumen of the catheter, the intermediate aperture situated between the distal aperture and a proximal aperture in the guidewire lumen;

(b) removing the first guidewire;

(c) movably closing the intermediate aperture in the guidewire lumen to prevent exit through the intermediate aperture; and (d) loading a second guidewire through the proximal aperture to the distal end of the guidewire lumen.

15. The method of claim 14, wherein the step of closing the intermediate aperture comprises moving a sleeve relative to the guidewire lumen, thereby closing the intermediate aperture.

16. The method of claim 15, wherein the proximal end of the sleeve is attached to a fitting, the fitting having a guide for indicating the relative positions of the sleeve and the guidewire lumen, thereby indicating when said intermediate aperture is open and closed.

17. The method of claim 14, wherein the portion of the guidewire lumen proximal to the intermediate aperture has a removable core member to enhance pushability of the catheter thereby aiding in positioning of the catheter, and after such positioning the core member being removed from the guidewire lumen prior to loading of the second guidewire.

18. The method of claim 14, wherein the steps of closing the intermediate aperture and loading the second guidewire move a flexible flap adjacent to the intermediate aperture, thereby closing the intermediate aperture.

19. The method of claim 18, wherein the portion of the guidewire lumen proximal to the intermediate aperture has a removable core member to enhance pushability of the catheter, thereby aiding in positioning of the catheter, and after such positioning the core member being removed from the guidewire lumen prior to loading of the second guidewire.

20. The method of claim 14, further comprising the steps of:

(a) removing the second guidewire from the guidewire lumen;

(b) movably opening the intermediate aperture in the guidewire lumen; and (c) loading a third guidewire through the intermediate and distal apertures.

21. A method for converting a catheter from an over-the-wire configuration to a rapid exchange configuration, comprising:

(a) removing a first guidewire from a guidewire lumen of the catheter, the first guidewire prior to removal extending between a proximal aperture in the guidewire lumen and the distal end of the guidewire lumen;

(b) movably opening an intermediate aperture in the guidewire lumen, the intermediate aperture situated between a distal aperture and the proximal aperture in the guidewire lumen; and (c) loading a second guidewire through the intermediate and distal apertures.

22. The method of claim 21, wherein the step of opening the intermediate aperture comprises moving a sleeve relative to the guidewire lumen, thereby opening the intermediate apertures.

23. The method of claim 22, wherein the proximal end of the sleeve is attached to a fitting, the fitting having a guide for indicating the relative positions of the sleeve and the guidewire lumen, thereby indicating when said intermediate aperture is open and closed.

24. The method of claim 21, further comprising the step of inserting a core member into the portion of the guidewire lumen proximal to the intermediate aperture, the core member providing enhanced pushability of the catheter after removal of the first guidewire.

25. The method of claim 21, wherein the step of opening the intermediate aperture comprises moving a flexible flap adjacent to the intermediate aperture, thereby opening the intermediate aperture.

* * * * *